United States Patent [19]
Katz et al.

[11] Patent Number: 5,135,740
[45] Date of Patent: Aug. 4, 1992

[54] POROUS PARTICLES IN PREPARATIONS INVOLVING IMMISCIBLE PHASES

[75] Inventors: Martin Katz, Menlo Park; Chung-Heng Cheng, San Jose, both of Calif.

[73] Assignee: Advanced Polymer Systems, Inc., Redwood City, Calif.

[21] Appl. No.: 418,776

[22] Filed: Oct. 2, 1989

Related U.S. Application Data

[63] Continuation-in-part of Ser. No. 185,204, Apr. 22, 1988, abandoned.

[51] Int. Cl.$^5$ .................... A61K 7/00; A61K 7/40; A01N 25/00
[52] U.S. Cl. .................... 424/401; 424/59; 424/76.1; 424/405; 424/409
[58] Field of Search ............. 424/78, 81, 487, 484, 424/489, 401, 405, 409, 59, 76.1

[56] References Cited

U.S. PATENT DOCUMENTS

| | | | |
|---|---|---|---|
| 3,758,686 | 9/1973 | Sieger et al. | 514/174 |
| 4,256,609 | 3/1981 | Dale et al. | 252/455 |
| 4,282,216 | 8/1981 | Rovee et al. | 514/179 |
| 4,336,070 | 6/1982 | Koghugi | 106/122 |
| 4,415,544 | 11/1983 | Kokotailo et al. | 423/328 |
| 4,435,524 | 3/1984 | Dinbergs | 428/402 |
| 4,478,818 | 10/1984 | Shell et al. | 424/78 |
| 4,542,069 | 9/1985 | Mauz et al. | 428/402 |
| 4,590,068 | 5/1986 | Berthet et al. | 428/402 |
| 4,690,825 | 9/1987 | Won | 424/501 |
| 4,818,542 | 4/1989 | DeLuca et al. | 424/491 |

FOREIGN PATENT DOCUMENTS

| | | |
|---|---|---|
| 0306236 | 8/1988 | European Pat. Off. |
| 502237 | 6/1930 | Fed. Rep. of Germany |
| 8905632 | 6/1989 | PCT Int'l Appl. |
| 302761 | 12/1928 | United Kingdom |
| 2166651 | 5/1986 | United Kingdom |

*Primary Examiner*—Howard E. Schain
*Assistant Examiner*—Choon P. Koh
*Attorney, Agent, or Firm*—Townsend and Townsend

[57] ABSTRACT

Immiscible phases, particularly polar and non-polar liquids, semi-solids or solids, are combined in a composition where one is finely dispersed throughout the other without reliance upon emulsifying agents to either create or stabilize the dispersion. The composition is formed by placing the discontinuous phase in the pores of solid inert porous particles, in which the pores are in the form of an interconnected network open to the exterior of the particles to provide interfacial contact with the continuous phase. The particles are then dispersed in the continuous phase. The concept is applicable to oil-in-water and water-in-oil type dispersions, and the disadvantages and shortcomings of emulsifying agents are entirely avoided.

30 Claims, No Drawings

POROUS PARTICLES IN PREPARATIONS INVOLVING IMMISCIBLE PHASES

This is a continuation-in-part of application Ser. No. 07/185,204, filed Apr. 22, 1988, now abandoned.

This invention relates to two-phase compositions in which the two phases are immiscible and one is finely dispersed throughout the other. Emulsions and colloidal suspensions are examples of such compositions, although the invention extends to all combinations of solids, semi-solids and liquids.

BACKGROUND OF THE INVENTION

The mixing of immiscible liquids to form a substantially uniform composition has been a classic problem for many industries. Examples of products where such mixtures are required are food products, cosmetics, toiletries, pharmaceuticals, paints and coatings. Such compositions extend from simple substances such as oil and water to complex substances. They may be characterized in many cases as non-polar hydrophobic materials combined with polar hydrophilic materials. These compositions are generally comprised of one of the phases in the form of discontinuous or discrete droplets dispersed through the other which forms the continuous phase, for example oil-in-water or water-in-oil. Critical to the uniformity of these compositions is the formation of droplets of very small size and a means of maintaining them in dispersed form, minimalizing any tendency to cause coalescence and thus separation of the phases.

The emulsion technology which has been created to address these difficulties is extensive and highly developed. Central to this technology is the use of such additives as surface active agents and detergents to form the droplets. The action of these additives is frequently supplemented by further additives such as protective colloids, gums, thickening agents and other classes of compounds which affect, alter and/or optimize the droplet size as well as the viscosity and stability of the emulsion.

The use of surface active agents requires special care for a number of reasons due to their chemical nature. During the manufacturing stages of the emulsion product, surface active agents raise considerations regarding their solubility, stability under varying conditions of temperature and pH, their frequent tendency to cause inversion of the phases, and their tendency to cause foaming, for example. Handling of surface active agents also requires special caution in many cases since they present potential health hazards upon inhalation and skin contact. Similar problems arise in end use of the finished products -- those requiring contact with human skin for utilitarian, industrial, cosmetic, toiletry or pharmaceutical purposes have produced stinging, irritation or sensitization for which the surface active agents have been implicated.

Oil-in-water type emulsions are often used for cosmetic and toiletry products. Such emulsions generally include mineral oils, vegetable oils, silicones, waxes, esters or the like as the internal phase, dispersed in aqueous solution, glycols or polyols.

Water-in-oil type emulsions encounter stability problems in much the same manner as the oil-in-water type. Such emulsions generally include aqueous solutions or glycols or polyols as the internal phase, dispersed in mineral oils, vegetable oils, silicones, waxes, esters or the like. Certain preparations involve the use of propylene glycol and/or propylene carbonate dispersed in petrolatum or liquid petrolatum. Emulsifying agents such as lanolin derivatives and cholesterol have been used. Unfortunately, the resulting emulsions are relatively unstable and tend to bleed and separate.

SUMMARY OF THE INVENTION

The present invention provides means for dispersing a first phase throughout a second with which the first is substantially immiscible, in a controlled and stable manner without reliance upon an emulsifying agent. In accordance with this invention, the internal or dispersed phase is retained within the pores of porous solid particles which are dispersed throughout the external or discontinuous phase. The particles are microscopic in size and contain a substantially continuous network of pores, interconnected and open to the exterior of the particles. The internal phase is retained in the pores while at the same time held in contact with the external phase through the pore openings. The dispersion of the internal phase throughout the external phase is thus controlled by the particles, which maintain the separation of the phases and prevent the coalescence of the internal phase. Control of the amount of particles present and the physical characteristics of the particles, such as their pore volume and pore size distribution are the means by which the dispersion itself is controlled, and further provide means of controlling the degree of actual interfacial contact between the two phases. For applications or compositions where controlled release or release on demand is a benefit, the formulations of the present invention provide a degree of control not heretofore seen. External forces such as rubbing or mixing, and externally applied conditions such as heating or the lowering of ambient pressure may be used to stimulate the release of the internal phase from the particle pores, increasing its dispersion into the external phase and also its release when desired to the surroundings.

The invention may be incorporated into a wide range of applications, both water-in-oil type and oil-in-water type dispersions, in products which are liquid, semi-solid or solid. In each case, a dispersion of high stability is achieved without the problems associated with surface active or other emulsifying agents and with added features of dispersion and release control. Further aspects and advantages of the invention will become apparent from the following description.

DETAILED DESCRIPTION OF THE INVENTION AND PREFERRED EMBODIMENTS

The particles used in connection with the present invention are open-pore, chemically and biologically inert particles. In particular, both the internal and dispersed phase or the external or continuous phase are inert with respect to the particles. The pores are interconnected and open to the particle surface to an extent that substantially full communication is provided between the internal pore space and the exterior of the particle.

In their most convenient form, the particles are generally spherical in shape, due to the use of suspension polymerization as a preferred method of preparation. While the particles may vary widely in size, those falling within the range of about one to about 100 microns in diameter, preferably from about 10 to about 40 microns, will provide the best results. Microspheres within these size ranges are appealing from an aesthetic point of view by imparting a smooth feel to the touch.

The pore dimensions within the particles may also vary widely, with optimum dimensions depending on the chemical characteristics of the polymers used as well as the type of dispersion ultimately sought. Different systems may thus have different optimum ranges of pore volume distribution to obtain the most desirable properties for the overall formulation. In general, however, best results are obtained with total pore volumes ranging from about 0.01 to about 4.0 cc/g. preferably from about 0.1 to about 2.0; surface areas ranging from about 1 to about 500 m$^2$/g, preferably from about 20 to about 200; and average pore diameters ranging from about 0.001 to about 3.0 micron, preferably from about 0.003 to about 1.0 micron. Following conventional methods of measuring and expressing pore sizes, the pore diameters are measured by techniques such as nitrogen adsorption isotherms or mercury intrusion and are based on the model of a pore of cylindrical shape.

The particles are conveniently formed by suspension polymerization in a liquid-liquid system. In general, a solution containing monomers and a polymerization catalyst (if used) is formed which is immiscible with water. An inert liquid fully miscible with the solution but immiscible with water is included in the solution. The solution is then suspended in an aqueous solution, which generally contains additives such as surfactants and dispersants to promote the suspension. Once the suspension is established with discrete droplets of the desired size, polymerization is effected (typically by activating the reactants by either increased temperature or irradiation). Once polymerization is complete, the resulting solid particles are recovered from the suspension. The particles are solid porous structures, the polymer having formed around the inert liquid, thereby forming the pore network. The liquid has accordingly served as a porogen, or pore-forming agent, and occupies the pores of the formed beads.

In certain cases, the substance forming the internal or dispersed phase of the final product may itself serve as the porogen, in which case the porous particles recovered from the suspension immediately after polymerization are substantially ready for use, following removal of surface moisture, and any further processing steps of this nature. In these cases, particle formation and incorporation of the liquid used as the internal phase are performed in a single step. This may accordingly be termed a one-step procedure. Internal phase, liquids which can be used in this manner are those which meet the following criteria:

1. They are either fully miscible with the monomer mixture or capable of being made fully miscible by the addition of a minor amount of non-water-miscible solvent;
2. They are immiscible with water. or at most only slightly soluble; and
3. They are inert with respect to the monomers, and stable when in contact with any polymerization catalyst used and when subjected to any conditions needed to induce polymerization (such as temperature and radiation).

For internal phase liquids which do not meet these criteria, their placement inside the pores may be achieved by impregnation of preformed dry porous polymer beads. The product is thus prepared in two steps performed in sequence, the polymerization being performed first with a substitute porogen which is then removed and replaced by the final liquid. Materials suitable as substitute porogens will be liquid substances which meet the above criteria and which have the further characteristic of being readily extracted from the pore network of the beads once polymerization is complete. This covers a wide range of substances, notably inert. nonpolar organic solvents. Some of the most convenient examples are alkanes, cycloalkanes, and aromatics. Examples of such solvents are alkanes of 5 to 12 carbon atoms, straight or branched chain, cycloalkanes of 5 to 8 carbon atoms, benzene, and alkyl-substituted benzenes such as toluene and the xylenes. Porogens of other types include $C_4$-$C_{20}$ alcohols, perfluoro polyethers, and silicone oils. Examples of silicone oils are polydimethylcyclosiloxane, hexamethyldisiloxane, cyclomethicone, dimethicone, amodimethicone, trimethylsilylamodimethicone, polysiloxane-polyalkyl copolymers (such as stearyl dimethicone and cetyl dimethicone), dialkoxydimethylpolysiloxanes (such as stearoxy dimethicone), polyquaternium 21, dimethicone propyl PG-Betaine, dimethicone copolyol and cetyl dimethicone copolyol.

Once polymerization is complete, the porogen may be removed by solvent extraction, evaporation, or similar conventional operations.

A further advantage of the use of this two-step process is that it permits the removal of unwanted species from the polymerized structures prior to impregnation with the adjuvants. Examples of unwanted species include unreacted monomers, residual catalyst, and surface active agents and/or dispersants remaining on the sphere surfaces. A further advantage of this technique is that it permits one to select the amount and type of porogen as a means of controlling the pore characteristics of the finished bead. One is thus no longer bound by the limitations of the final internal phase as they affect the structure of the particle itself. This also permits partial rather than full filling of the pores with the internal phase, and further control over pore size and distribution by selection among swelling and non-swelling porogens.

Extraction of the porogen and its replacement with (i.e., impregnation of the dry bead with) the internal phase in the two-step procedure may be effected in a variety of ways, depending on the chemical nature of the porogen and its behavior in combination with that of the other species present. The particles are first recovered from the suspension by filtration, preferably using vacuum filtration apparatus (such as a Buechner funnel). The beads are then washed with an appropriate solvent to remove organic species not bound to the polymer, including surfactants having deposited on the bead surfaces from the aqueous phase, unreacted monomers and residual catalysts, and the porogen itself. An example of such a solvent is isopropanol, either alone or in aqueous solution. Once washing is complete, the solvent itself is removed by drying, preferably in a vacuum.

In certain cases, an alternative method of extraction may be used i.e., where the porogen, unreacted monomer and water will form an azeotrope. In these cases, steam distillation is an effective way of extracting porogen from the beads. This again may be followed by drying under vacuum.

Once the particles are rendered dry and free of the substitute porogen and any unwanted organic materials, they are impregnated with the internal phase according to conventional techniques. The most convenient such technique is contact absorption, aided by solvents if necessary to enhance the absorption rate.

The polymerization process and the various parameters and process conditions involved can be selected and adjusted as a means of controlling the pore characteristics and consequently the capacity of and interfacial contact provided by the ultimate product. For example, proper selection of the cross-linking means, the amount and type of cross-linking agent, and the amount and type of porogen are means of attaining such control. Certain polymerization conditions may also be varied to such effect, including temperature, degree of radiation where used, degree of agitation and any other factors affecting the rate of the polymerization reaction.

Cross-linking in the polymer formation is a major means of pore size control. Monomers which may be polymerized to produce cross-linked polymer beads in accordance with the present invention include polyethylenically unsaturated monomers, i.e., those having at least two sites of unsaturation, and monoethylenically unsaturated monomers in combination with one or more polyethylenically unsaturated monomers. In the latter case, the percentage of cross-linking may be controlled by balancing the relative amounts of monoethylenically unsaturated monomer and polyethylenically unsaturated monomer.

Monoethylenically unsaturated monomers suitable for preparing polymer beads for the polymer delivery system include ethylene, propylene, isobutylene, diisobutylene, styrene, ethylvinylbenzene, vinyltoluene, and dicyclopentadiene; esters of acrylic and methacrylic acid, including the methyl, ethyl, propyl, isopropyl, butyl, sec-butyl, tert-butyl, amyl, hexyl, octyl, ethylhexyl decyl, dodecyl, cyclohexyl, isobornyl, phenyl, benzyl, alkylphenyl, ethoxymethyl, ethoxyethyl, ethoxypropyl, propoxymethyl, propoxyethyl, propoxypropyl, ethoxyphenyl, ethoxybenzyl, and ethoxycyclohexyl esters: vinyl esters, including vinyl acetate, vinyl propionate, vinyl butyrate and vinyl laurate; vinyl ketones, including vinyl methyl ketone, vinyl ethyl ketone, vinyl isopropyl ketone, and methyl isopropenyl ketone, vinyl ethers, including vinyl methyl ether, vinyl ethyl ether, vinyl propyl ether, and vinyl isobutyl ether; and the like.

Polyethylenically unsaturated monomers which ordinarily act as though they have only one unsaturated group, such as isoprene, butadiene and chloroprene, may be used as part of the monoethylenically unsaturated monomer content.

Polyethylenically unsaturated cross-linking monomers suitable for preparing such polymer beads include diallyl phthalate, ethylene glycol diacrylate, ethylene glycol dimethacrylate, trimethylolpropanetrimethacrylate, divinylsulfone; polyvinyl and polyallyl ethers of ethylene glycol, of glycerol, of pentaerythritol, of diethyleneglycol, of monothio- and dithio-derivatives of glycols, and of resorcinol; divinylketone, divinylsulfide, allyl acrylate, diallyl maleate, diallyl fumarate, diallyl succinate, diallyl carbonate, diallyl malonate, diallyl oxalate, diallyl adipate, diallyl sebacate, divinyl sebacate, diallyl tartrate, diallyl silicate, triallyl tricarballylate, triallyl aconitate, triallyl citrate, triallyl phosphate, divinyl naphthalene, divinylbenzene, trivinylbenzene; alkyldivinylbenzenes having from 1 to 4 alkyl groups of 1 to 2 carbon atoms substituted on the benzene nucleus; alkyltrivinylbenzenes having 1 to 3 alkyl groups of 1 to 2 carbon atoms substituted on the benzene nucleus; trivinylnaphthalenes, and polyvinylanthracenes.

Particularly preferred polymer systems of the present invention are formed by the copolymerization of styrene and divinylbenzene, vinyl stearate and divinylbenzene, or methylmethacrylate and ethylene glycol dimethylmethacrylate. Usually, the monoethylenically unsaturated monomer will be present at from about 20% to 80% of the monomer mixture, with the polyethylenically unsaturated monomer forming the remainder of the mixture. Particularly preferred is the styrene-divinylbenzene polymeric bead which consists essentially of a hydrocarbon backbone with benzene rings and which is substantially completely free from reactive groups.

Examples of organic solvents in which substances serving as the internal phase can be dissolved to facilitate absorption include liquid petrolatum, petroleum ether, ethanol (especially for menthol and thymol) higher alcohols (especially for camphor), isopropyl myristate, diisopropyl adipate, and mineral oil. The solvent can then be evaporated or, if desired, retained together with the absorbed substance within the pores. Other formulating materials, such as carriers or adjuvants and the like can also be present, and will be incorporated into and onto the beads together with the substances of interest and any other materials present.

The retained phase should comprise between approximately 5% and approximately 65% of the total weight of the impregnated beads, although the actual amount may vary. As for the dispersion itself, the retained phase plus solid particles will generally comprises from about 1% to about 50% of the dispersion on a volume basis, preferably from about 5% to about 25%.

The present invention extends to systems where both the phase retained in the pores of the solid particles and the phase in which the solid particles are dispersed may be either solid, liquid or semi-solid. Solids will include waxes and similar materials which can be softened or melted for processing purposes, such as by heating. Lipsticks and other lip applications are examples of solid materials. Semi-solids will include gels, ointments and pastes and similar materials. Liquids will include oils, lotions, creams and solutions, both aqueous and nonaqueous.

Systems where the internal phase (i.e., the phase retained inside the particle pores) is a solid may be prepared by first melting the solid and impregnating the particles with it while it is melted, then cooling it to permit it to solidify; or by dissolving the solid in a solvent for impregnation purposes, then evaporating the solvent. Release of a solid impregnant from the pores may be effected upon command by heat or exposure to a solvent, depending on the nature of the impregnant. Systems where the external phase is a solid may be prepared in a similar manner.

Additives may be included in the continuous phase for a variety of purposes. Gums or thickening agents, for example, may be included to facilitate dispersion and prevent caking and settling. Examples of these are acacia, tragacanth, chondrus, alginates, cellulose derivates (such as methyl cellulose, for example), Carbopol TM resins, Cab-O-Sil TM, polyvinyl pyrollidone, V-gum, and bentonites. These will also provide lubricity and viscosity. Viscosity can also be increased by the addition of such materials as further clays, silicas, waxes and polyethylene. Aqueous phases may be modified by the addition of agents for increasing or decreasing volatility and for serving as humectants. Examples are alcohols, glycols, polyols such as sorbitol, and sugars such as sucrose, fructose, and dextrose.

Oil-in-water type compositions in accordance with the invention may be used as a means of spreading a controlled amount of a functional oil over a wide expanse of an epidermal region, without the oily feel normally associated with formulations of these substances, and further avoiding the tacky-sticky stages which the formulation goes through between application and drying. Functional oils which can be applied in this manner cover a broad range of substances, including emollients, moisturizers, lubricants, sun screens, insect repellants, vitamins, fragrances, drugs, deodorants, pigments, and others. As indicated above, the aqueous phase may then be enhanced by the inclusion of volatile polar solvents to enhance volatility, humectants to enhance moisture retention, and gums or thickening agents to enhance uniformity.

Water-in-oil type compositions serve as a means of incorporating polar substances into non-polar substances, such as for example humectants into oil-based or lipid-based materials. Propylene glycol and/or propylene carbonate may thus be dispersed into liquid petrolatum without the use of lanolin or cholesterol, which normally serve as emulsifying agents. The propylene glycol or carbonate may also serve as a solvent for other polar functional substances such as corticosteroids, thereby providing a composition useful for clinical purposes such as vasoconstrictor activity.

In general, compositions in accordance with the present invention may enjoy a wide range of uses and applications, for such purposes as cosmetic and pharmaceutical purposes, and as toiletries, fragrances, household products (waxes, polishes, cleansers), industrial applications and more.

The following example is offered primarily for purposes of illustration, and is intended neither to limit nor define the invention in any manner.

EXAMPLE

This example illustrates the application of the present invention to the formation of a water-in-oil type emulsion. The example is that of a lipstick, in which the continuous phase is a solid wax-like material, and the purpose was to incorporate a humectant into the lipstick.

An aqueous humectant solution was prepared by combining the following ingredients in water:
glycerine
DL-panthenol
aqueous sodium lactate
aqueous sodium pyrrolidone carboxylic acid
The solution was then combined with porous beads averaging 25 microns in diameter. the beads having been formed by copolymerization of methyl methacrylate and ethylene glycol dimethacrylate, in accordance with techniques described in copending, commonly assigned U.S. patent application Ser. No. 07/091,641, filed Aug. 31, 1987. The beads had a pore volume of 0.31 cc/g, a surface area of 85.1 m$^2$/g, and an average pore diameter of 0.0146 micron. The relative amounts of humectant and beads were 75 parts and 175 parts by weight, respectively.

The impregnated beads were then combined with a lipstick mass, using for the latter a typical non-water-miscible composition containing beeswax combined with other waxes and oils. This was achieved by melting 4 parts by weight of the lipstick mass at 60°–70° C. and adding 0.08 parts by weight of the impregnated beads to the melt, followed by mixing until homogeneous. The result upon cooling was a lipstick which was homogeneous in appearance and feel and yet had humectant properties.

The foregoing description is intended primarily for purposes of illustration. It will be readily apparent to those skilled in the art that further variations and modifications in the implementation of the concepts described herein can be made without departing from the spirit and scope of the invention.

What is claimed is:

1. A composition comprising solid particles dispersed in a solid, semi-solid or liquid continuous phase, said solid particles each containing a substantially continuous network of pores open to the exterior of said particles with a substance substantially immiscible with said continuous phase retained in said pores, said substance and said continuous phase each being inert with respect to said solid particles and each being free of catalysts and unreacted species to form said solid particles.

2. A composition in accordance with claim 1 in which said solid particles have an average diameter of about one micron to about 100 microns.

3. A composition in accordance with claim 1 in which said solid particles have an average diameter of about 10 microns to about 40 microns.

4. A composition in accordance with claim 1 in which said solid particles have a total pore volume of about 0.01 cc/g to about 4.0 cc/g.

5. A composition in accordance with claim 1 in which said solid particles have a total pore volume of about 0.1 cc/g to about 2.0 cc/g.

6. A composition in accordance with claim 1 in which said solid particles have a surface area of about 1 m$^2$/g to about 500 m$^2$/g.

7. A composition in accordance with claim 1 in which said solid particles have a surface area of about 20 m$^2$/g to about 200 m$^2$/g.

8. A composition in accordance with claim 1 in which said solid particles have an average pore diameter of about 0.001 micron to about 3.0 microns.

9. A composition in accordance with claim 1 in which said solid particles have an average pore diameter of about 0.003 micron to about 1.0 micron.

10. A composition in accordance with claim 1 in which said solid particles are formed of a crosslinked polymer.

11. A composition in accordance with claim 10 in which said cross-linked polymer is a copolymer of styrene and divinylbenzene.

12. A composition in accordance with claim 10 in which said cross-linked polymer is a copolymer of methyl methacrylate and ethylene glycol dimethacrylate.

13. A composition in accordance with claim 1 in which said solid particles and said liquid comprise from about 1% to about 50% by volume of said dispersion.

14. A composition in accordance with claim 1 in which said solid particles and said liquid comprise from about 5% to about 25% by volume of said dispersion.

15. A composition in accordance with claim 1 in which said substance is a solid.

16. A composition in accordance with claim 1 in which said substance is a semi-solid.

17. A composition in accordance with claim 1 in which said substance is a liquid.

18. A composition comprising solid particles immersed in a solid continuous phase, said solid particles each containing a substantially continuous network of pores open to the exterior of said particles with a substance substantially immiscible with said solid continuous phase retained in said pores, said substance and said continuous phase each being inert with respect to said solid particles.

19. A composition comprising solid particles immersed in a semi-solid continuous phase, said solid particles each containing a substantially continuous network of pores open to the exterior of said particles with a substance substantially immiscible with said semi-solid continuous phase retained in said pores, said substance and said continuous phase each being inert with respect to said solid particles.

20. A composition comprising solid particles immersed in a liquid continuous phase selected from the group consisting of oils, lotions and creams, said solid particles each containing a substantially continuous network of pores open to the exterior of said particles with a substance substantially immiscible with said liquid continuous phase retained in said pores, said substance and said continuous phase each being inert with respect to said solid particles.

21. A composition in accordance with claim 1 in which said substance is a substantially non-polar hydrophobic liquid and said continuous phase is a substantially polar hydrophilic liquid.

22. A composition in accordance with claim 21 in which said substantially polar hydrophilic liquid is an aqueous liquid.

23. A composition in accordance with claim 22 in which said aqueous liquid is comprised of water combined with at least one member selected from the group consisting of volatilization-enhancing agents. humectants and thickening agents.

24. A composition in accordance with claim 21 in which said substantially non-polar hydrophobic liquid is a member selected from the group consisting of emollients, moisturizers, lubricants, sunscreens, insect repellents, vitamins, fragrances, drugs, deodorants and pigments.

25. A composition in accordance with claim 1 in which said substance is a substantially polar hydrophilic liquid and said continuous phase is a substantially non-polar hydrophobic liquid.

26. A composition in accordance with claim 25 in which said substantially polar hydrophilic liquid is a humectant.

27. A composition in accordance with claim 26 in which said humectant is a member selected from the group consisting of sugars, glycols and polyols.

28. A composition in accordance with claim 25 in which said substantially polar hydrophilic liquid is comprised of a polar solvent.

29. A composition in accordance with claim 25 in which said substantially polar hydrophilic liquid 30. A composition in accordance with claim 25 in which said substantially polar hydrophilic liquid is a solution of a corticosteroid in a polar solvent selected from the group consisting of propylene glycol and propylene carbonate, and said continuous phase is petrolatum.

* * * * *